(12) United States Patent
Poellmann et al.

(10) Patent No.: US 8,546,616 B2
(45) Date of Patent: Oct. 1, 2013

(54) POLYETHERAMINE MACROMONOMERS COMPRISING TWO NEIGHBORING HYDROXYL GROUPS AND THEIR USE FOR PRODUCING POLYURETHANES

(75) Inventors: Klaus Poellmann, Munich (DE); Juergen Muenter, Fellbach (DE)

(73) Assignee: Clariant Finance (BVI) Limited, Tortola (VG)

( * ) Notice: Subject to any disclaimer, the term of this patent is extended or adjusted under 35 U.S.C. 154(b) by 308 days.

(21) Appl. No.: 12/376,273

(22) PCT Filed: Jun. 13, 2007

(86) PCT No.: PCT/EP2007/005207
§ 371 (c)(1),
(2), (4) Date: Feb. 3, 2009

(87) PCT Pub. No.: WO2008/014844
PCT Pub. Date: Feb. 7, 2008

(65) Prior Publication Data
US 2009/0318656 A1    Dec. 24, 2009

(30) Foreign Application Priority Data
Aug. 3, 2006    (DE) .......................... 10 2006 036 220

(51) Int. Cl.
*C07C 213/00*    (2006.01)
*C07C 217/00*    (2006.01)

(52) U.S. Cl.
USPC ........... 564/508; 564/503; 564/504; 564/505; 564/506; 564/507; 564/474; 564/475

(58) Field of Classification Search
USPC .......................... 564/503–508, 474, 475, 479
See application file for complete search history.

(56) References Cited

U.S. PATENT DOCUMENTS

| | | | |
|---|---|---|---|
| 4,092,286 A | 5/1978 | Noll et al. | |
| 4,192,937 A | 3/1980 | Noll et al. | |
| 4,269,748 A | 5/1981 | Nachtkamp et al. | |
| 4,292,226 A | 9/1981 | Wenzel et al. | |
| 6,372,000 B1 * | 4/2002 | DeRosa et al. | 44/424 |

FOREIGN PATENT DOCUMENTS

| | | | |
|---|---|---|---|
| CA | 1129128 | | 8/1982 |
| DE | 2551094 | | 5/1977 |
| DE | 3049746 | | 11/1982 |
| DE | 102005006317 | * | 8/2006 |
| EP | 0043966 | | 12/1983 |
| EP | 0622378 | | 11/1994 |

OTHER PUBLICATIONS

Translation DE 102005006317 document.*
Houben-Weyl, Methoden der Organischen Chemie, Bd. E 20, vol. F, pp. 16591681.
J. W. Rosthauser, K. Nachtkamp, Journal of Coated Fabrics, 1986, 16, 3979.
R. Amoldus, Surf Coating 1990, 3, 179-198.
S. Dedrichs, European Coating, Journal, S. 565, 5, 2002.
H. Kayer, Dissertation, University of Hamburg, 2002.
R. A. Schutz, et al., J. Am. Chem. Soc., 1985, 107, 6659-6668.
English Abstract for EP0043966.
English Abstract for EP0622378.
International Search Report for PCT/EP2007/005207 dated Sep. 18, 2007.
Translation of International Preliminary Report of Patentability for PCT/EP2007/005207 dated Sep. 18, 2007.
Jung-Eun Yang, et al., "Preparation and Properties of Waterborne Polyurethane-Urea Anionomers. I. The Influence of the Degree of Neutralization and Counterion", J. of Applied Polymer Science, vol. 86, pp. 2375-2383, (2002).

* cited by examiner

*Primary Examiner* — Michael L Leonard
(74) *Attorney, Agent, or Firm* — Tod A. Waldrop

(57) ABSTRACT

The object of the invention are compounds of the formula (2) wherein $R^1$ is H, methyl or ethyl, $R^2$ is $C_1$- to $C_4$ alkyl, A is a $C_2$- to $C_4$ alkylene group, m is number from 10 to 400, n is 1, 2, 3, 4, or 5, a method for their production and their use in the production of polyurethane prepolymers.

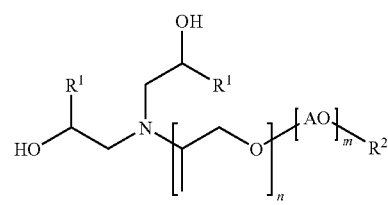

(2)

6 Claims, No Drawings

POLYETHERAMINE MACROMONOMERS COMPRISING TWO NEIGHBORING HYDROXYL GROUPS AND THEIR USE FOR PRODUCING POLYURETHANES

The present invention relates to Ω-(alkoxy)-α-N,N-dihydroxyalkylaminopolyalkylene glycols, and to their use for producing water-dispersible polyurethanes.

On account of their high resistance and simple application, polyurethane systems have acquired a broad application field in the paint, (surface) coating and textile industry sector. For reasons of environmental protection and occupational protection, in the recent past primarily solvent-free, water-dispersed polyurethane systems have been developed.

The production of aqueous polyurethane dispersions has been known for many years and is described in detail in a large number of publications (e.g. Houben-Weyl, Methoden der Organischen Chemie [Methods of organic chemistry], Volume E20, Part I, pp. 1659-1681; D. Dieterich, Prog. Org. Coat. 1981, 9, 281-330; J. W. Rosthauser, K. Nachtkamp, Journal of Coated Fabrics 1986, 16, 39-79; R. Arnoldus, Surf. Coat. 1990, 3 (Waterborne Coat.), 179-198).

Aqueous polyurethane dispersions consist of polyurethane polymers or polyurethane-polyurea polymers which include both urethane groups and also urea groups and are accessible by polyaddition reactions of polyols, polyisocyanates and polyamines. Firstly, polyurethane prepolymers are produced from the polyols and the polyisocyanates; these are then dispersed in the aqueous phase and chain-extended with polyamines to form the polyurethane-polyurea polymers. Additionally, the polyurethane polymers have to comprise an adequate amount of hydrophilic groups which ensure the stabilization in the aqueous phase. These hydrophilic groups are anionic, cationic or nonionic groups or a combination of the aforementioned groups.

In order to be able to dispense with the use of external emulsifiers, the production of stable aqueous polyurethane dispersions is possible only with the help of suitable comonomers which, by virtue of their hydrophilicity, permit a stable aqueous dispersion of polyurethane prepolymers. (S. Dedrichs, European Coating Journal p. 565, 5, 2002, Noll, DE-A-25 51 094). In order to achieve complete incorporation of the hydrophilic comonomers into the hydrophobic polyurethane prepolymer, diols with hydrophilic radicals, such as, for example, dimethylolpropanoic acid (DMPA), are used. In this case, the dispersion is stabilized following neutralization of the carboxylic acid side groups through electrostatic repulsion of the carboxylate groups incorporated into the prepolymer. (H. Kager, Dissertation, Uni Hamburg 2002, Jung-Eun Yang, Journal of Applied Polymer Science 86, 9, p. 2375).

Besides the electrostatic stabilization through carboxylate groups, aqueous polyurethane dispersions are also produced through nonionic, hydrophilic, sterically stabilizing groups. The attainment of this steric stabilization of polyurethane dispersions therefore requires long, hydrophilic side chains which do not react with isocyanates and which, like DMPA, can be incorporated into the polyurethane prepolymer via two hydroxyl groups (DE-A-25 51 094). Polyethers (polyalkylene glycols) with two free closely neighboring hydroxyl groups on the same end of the molecule and a long polyalkylene side chain provided with an alkoxy end according to formula 1 below have proven to be particularly suitable in this regard. (S. Dedrichs, European Coating Journal p. 565, 5, 2002, DE 30 49 746 A1).

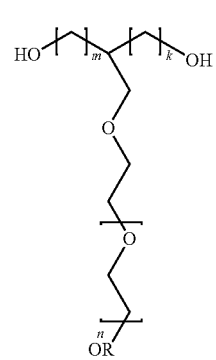

Here, $m=k=1$; $n>=20$ and R=alkyl or alkyl-N—C=O.

However, the production of such systems is very complex and expensive and proceeds over 4 stages starting from trifunctional alcohols such as glycerol or trimethylolpropane (DE-A-30 49 746, EP-A-0 043 966):

stage 1: preparation of a hydroxymethyl-1,3-dioxolane from the trifunctional alcohol stage 2: reaction of the alkaline hydroxymethyl-1,3-dioxolane with an alkylene oxide stage 3: reaction of the Ω-hydroxy-α-(1,3-dioxolano)polyalkylene glycol with an alkyl halide or an alkyl monoisocyanate stage 4: acid-catalyzed cleavage of the 1,3-dioxolane ring to give the diol.

It is a disadvantage of this process that in the etherification in stage 3 large amounts of alkali metal halides are produced as by-product which interfere in the further reaction to give polyurethane prepolymers and are difficult to remove. Moreover, in the case of an incomplete reaction in stage 3, besides the target diols, trihydroxy-functional polyalkylene glycols can be formed as by-products which, upon polymerization into the polyurethane prepolymer dispersion, can cause crosslinking and thus insolubilities (EP-A-00 43 966). The production, described in DE-A-25 14 513, of diisocyanates with polyalkylene glycol side chains by reacting triisocyanates with a monohydroxy-functional polyalkylene glycol gives rise to the problem of the formation of crosslinking triisocyanates and/or of the presence of monohydroxy- or monoisocyanate-functional components, depending on the selected stoichiometry. Here too, triisocyanate-functional components potentially cause crosslinking, but monohydroxy- or monoisocyanate-functional components cause chain termination of the linear PU polymers.

It was therefore an object of the present invention to find an Ω-(alkoxy)-α-dihydroxyalkylpolyalkylene glycol which can be prepared easily and cost-effectively and which does not have the aforementioned disadvantages during production and application.

The Ω-(alkoxy)-α-dihydroxyalkylpolyalkylene glycol should be able to be incorporated in a suitable manner into polyurethane prepolymer dispersions and ensure the stability of the aqueous prepolymer dispersions.

The invention thus provides compounds of formula 2

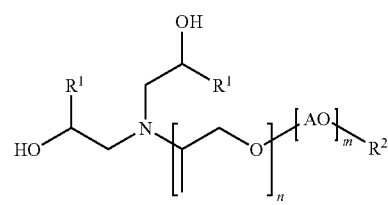

in which
R¹ is H, methyl or ethyl,
R² is C₁- to C₄-alkyl,
A is a C₂- to C₄-alkylene group,
m is a number from 1 to 400
n is 1, 2, 3, 4 or 5.

The invention further provides a process for producing polyurethane prepolymers by reacting compounds of formula 2 with a polyisocyanate and optionally with further polyols or polyamines.

The invention further provides a process for producing polyurethane polymers by
a) reacting a compound of formula 2 with a polyisocyanate and optionally with further polyols or polyamines to give a polyurethane prepolymer, and
b) reacting the resulting polyurethane prepolymer in aqueous medium with a polyamine to give a polyurethane polymer.

The invention further provides polyurethane prepolymers obtainable by the reaction of a compound of formula 2 with an isocyanate of the formula X(NCO)$_p$, in which p is a number from 2 to 4 and X is an aliphatic, cycloaliphatic, aromatic or araliphatic hydrocarbon radical.

The invention further provides polyurethane polymers obtainable by the reaction of a compound of formula 2 with an isocyanate of the formula X(NCO)$_p$, in which p is a number from 2 to 4 and X is an aliphatic, cycloaliphatic, aromatic or araliphataic hydrocarbon radical, and the subsequent reaction of the resulting polyurethane prepolymer in an aqueous medium with a polyamine of the formula Y(NH$_2$)$_q$, in which Y is an aliphatic, cycloaliphatic, aromatic or araliphatic hydrocarbon radical, and q is a number from 2 to 4.

The invention further provides the use of the compounds of formula 2 for producing polyurethane prepolymers by reacting the compound of formula 2 with an isocyanate of the formula X(NCO)$_p$, in which p is a number from 2 to 4 and X is an aliphatic, cycloaliphatic, aromatic or araliphatic hydrocarbon radical.

The invention further provides the use of the compounds of formula 2 for producing polyurethane polymers by reacting the compound of formula 2 with an isocyanate of the formula X(NCO)$_p$, in which p is a number from 2 to 4 and X is an aliphatic, cycloaliphatic, aromatic or araliphatic hydrocarbon radical, and the resulting polyurethane prepolymer is reacted in an aqueous medium with a polyamine of the formula Y(NH$_2$)$_q$, in which Y is an aliphatic, cycloaliphatic, aromatic or araliphatic hydrocarbon radical, and q is a number from 2 to 4.

In the oxalkylene group given by (A-O)$_m$, the total number of oxalkylene units is preferably between 3 and 250, in particular between 5 and 200. The oxalkylene chain may be a homopolymer or block copolymer chain which has alternating blocks of different oxalkylene units. It may also be a chain with a random sequence of the oxalkylene units, or a chain with random and blockwise chain sections. The oxalkylene units are preferably only oxethylene units, or a mixture of oxethylene and oxypropylene units, where preferably at least 50 mol % of the radicals (A-O) are oxethylene radicals.

In a further preferred embodiment, -(A-O)$_m$—R² is an oxalkylene chain of the formula

—(CH$_2$—CH$_2$—O)$_b$—(CH(CH$_3$)—CH$_2$—O)$_a$—R² in which
a is a number from 0 to 300, preferably 1 to 50
b is a number from 3 to 300, preferably 5 to 200
and R² has the meaning given above.
Preferably, R¹ is hydrogen.
Preferably, R² is methyl.
In a further preferred embodiment, R¹ is hydrogen and R² is methyl.
In a further preferred embodiment, n is 2, 3 or 4.
The compounds of formulae 2 are also referred to below as Ω-alkoxypolyetheraminediols.

The process for producing the Ω-alkoxypolyetheraminediols and also the production of polyurethane dispersions therewith are described in more detail below and illustrated by reference to examples.

The Ω-alkoxypolyetheraminediols can be produced from commercially available α-amino-Ω-alkoxypolyalkylene glycols (DE-A-16 43 426), or use is made of α-amino-Ω-alkoxypolyalkylene glycols produced specifically for this purpose from α-hydroxy-Ω-alkoxypolyalkylene glycols according to the process described in DE-A-16 43 426 by replacing, in an aminolysis reaction, the α-hydroxy group by a primary amino group. This primary amino group is then reacted, without the addition of an alkoxylation catalyst, with precisely 2 mol of alkylene oxide to give the dihydroxyalkylamino group.

The degree of solubility in water, defined by the cloud point in accordance with DIN EN 1890, of the Ω-alkoxypolyetheraminediols, and also the degree of their hydrophilizing and dispersing effect can be adjusted through the ratio and number of oxalkylene units (AO)$_m$, preferably of ethylene oxide to propylene oxide.

The isocyanates of the formula X(NCO)$_p$ are preferably those in which X is an aliphatic hydrocarbon radical having 4 to 12 carbon atoms, a cycloaliphatic or aromatic hydrocarbon radical having 6 to 15 carbon atoms or an araliphatic hydrocarbon radical having 7 to 15 carbon atoms.

Examples of such diisocyanates are tetramethylene diisocyanate, hexamethylene diisocyanate, dodecamethylene diisocyanate, 1,4-diisocyanatocyclohexane, 1-isocyanato-3,5,5-trimethyl-5-isocyanatomethylcyclohexane (IPDI), 2,2-bis(4-isocyanatocyclohexyl)propane, trimethylhexane diisocyanate, 1,4-diisocyanatobenzene, 2,4-diisocyanatotoluene, 2,6-diisocyanatotoluene, 4,4'-diisocyanatodiphenylmethane, 2,4'-diisocyanatodiphenylmethane, p-xylylene diisocyanate, tetramethylxylylene diisocyanate (TMXDI), the isomers of bis(4-isocyanatocyclohexyl)methane (HMDI), such as the trans/trans, the cis/cis and the cis/trans isomers, and also mixtures consisting of these compounds.

Mixtures of these isocyanates which are of importance are particularly the mixtures of the respective structural isomers of diisocyanatotoluene and diisocyanatodiphenylmethane; in particular, the mixture of 80 mol % of 2,4-diisocyanatotoluene and 20 mol % of 2,6-diisocyanatotoluene is suitable. Furthermore, the mixtures of aromatic isocyanates such as 2,4-diisocyanato-toluene and/or 2,6-diisocyanatotoluene with aliphatic or cycloaliphatic isocyanates, such as hexamethylene diisocyanate or IPDI, are particularly advantageous, the preferred mixing ratio of the aliphatic isocyanates to aromatic isocyanates being 4:1 to 1:4.

To construct the polyurethanes, compounds which can be used are, apart from those mentioned above, also isocyanates which, besides the free isocyanate groups, carry further capped isocyanate groups, e.g. uretdione groups.

The polyamines used for the reaction of the polyurethane prepolymers to give the polyurethane polymers are those in which Y is an aliphatic hydrocarbon radical having 4 to 12 carbon atoms, a cycloaliphatic or aromatic hydrocarbon radical having 6 to 15 carbon atoms or an araliphatic hydrocarbon radical having 7 to 15 carbon atoms. Preferred amines are polyfunctional amines of the molecular weight range from 32 to 500 g/mol, preferably from 60 to 300 g/mol, which contain at least two amino groups, selected from the group of primary and secondary amino groups. Examples thereof are diamines such as diaminoethane, diaminopropanes, diaminobutanes, diaminohexanes, piperazine, 2,5-dimethylpiperazine, amino-3-aminomethyl-3,5,5-trimethylcyclohexane (isophoronediamine, IPDA), 4,4'-diaminodicyclohexylmethane, 1,4-diaminocyclohexane, aminoethylethanolamine, hydrazine, hydrazine hydrate or triamines such as diethylenetriamine or 1,8-diamino-4-aminomethyloctane.

The amines can also be used in blocked form, e.g. in the form of the corresponding ketimines (see e.g. CA-A-1 129 128), ketazines (cf. e.g. U.S. Pat. No. 4,269,748) or amine salts (see U.S. Pat. No. 4,292,226). Oxazolidines, as are used, for example, in U.S. Pat. No. 4,192,937, are also capped polyamines which can be used for producing the polyurethanes according to the invention for the chain extension of the prepolymers. Preference is given to using mixtures of diamines and triamines, particularly preferably mixtures of isophoronediamine (IPDA) and diethylenetriamine (DETA).

The described polyamines are likewise suitable for use in the reaction of the compound of formula 2 with a polyisocyanate.

Diols are optionally used in the reaction of the compounds of formula 2 with polyisocyanates to give the polyurethane prepolymer and in the production of the polyurethane polymers.

The diols are in particular polyester polyols, which are known, for example, from Ullmanns Encyclopedia of Industrial Chemistry, 4th Edition, Volume 19, pp. 62 to 65. Preference is given to using polyester polyols which are obtained by reacting dihydric alcohols with dibasic carboxylic acids. Instead of the free polycarboxylic acids, it is also possible to use the corresponding polycarboxylic anhydrides or corresponding polycarboxylic acid esters of lower alcohols or mixtures thereof for producing the polyester polyols. The polycarboxylic acids may be aliphatic, cycloaliphatic, araliphatic, aromatic or heterocyclic and be optionally substituted, e.g. by halogen atoms, and/or unsaturated. Examples thereof which may be mentioned are:

suberic acid, azelaic acid, phthalic acid, isophthalic acid, phthalic anhydride, tetrahydrophthalic anhydride, hexahydrophthalic anhydride, tetrachlorophthalic anhydride, endomethylenetetrahydrophthalic anhydride, glutaric anhydride, maleic acid, maleic anhydride, fumaric acid, dimeric fatty acids. Preference is given to dicarboxylic acids of the formula HOOC—$(CH_2)_y$—COOH, where y is a number from 1 to 20, preferably an even number from 2 to 20, e.g. succinic acid, adipic acid, sebacic acid and dodecanedicarboxylic acid.

Suitable polyhydric alcohols are, for example, ethylene glycol, propane-1,2-diol, propane-1,3-diol, butane-1,3-diol, butene-1,4-diol, butyne-1,4-diol, pentane-1,5-diol, neopentyl glycol, bis(hydroxymethyl)cyclohexanes such as 1,4-bis(hydroxy-methyl)cyclohexane, 2-methylpropane-1,3-diol, methylpentanediols, also diethylene glycol, triethylene glycol, tetraethylene glycol, polyethylene glycol, dipropylene glycol, polypropylene glycol, dibutylene glycol and polybutylene glycols.

Preference is given to alcohols of the formula HO—$(CH_2)_x$—OH, where x is a number from 1 to 20, preferably an even number from 2 to 20. Examples thereof are ethylene glycol, butane-1,4-diol, hexane-1,6-diol, octane-1,8-diol and dodecane-1,12-diol. Furthermore, preference is given to neopentyl glycol. Furthermore, polycarbonatediols are also suitable, as can be obtained, for example, by reacting phosgene with an excess of the low molecular weight alcohols specified as synthesis components for the polyester polyols.

Also suitable are polyesterdiols based on lactone, which may be homopolymers or mixed polymers of lactones, preferably addition products, having terminal hydroxyl groups, of lactones onto suitable difunctional starter molecules. Suitable lactones are preferably those which are derived from compounds of the formula HO—$(CH_2)_z$—COOH, where z is a number from 1 to 20 and a H atom of a methylene unit may also be substituted by a $C_1$- to $C_4$-alkyl radical. Examples are ε-caprolactone, β-propiolactone, γ-butyrolactone and/or methyl-ε-caprolactone, and mixtures thereof. Suitable starter components are, for example, the low molecular weight dihydric alcohols specified above as synthesis component for the polyesterpolyols. The corresponding polymers of ε-caprolactone are particularly preferred. Lower polyesterdiols or polyetherdiols can also be used as starters for the preparation of the lactone polymers. Instead of the polymers of lactones, it is also possible to use the corresponding, chemically equivalent polycondensates of the hydroxycarboxylic acids corresponding to the lactones.

In addition, suitable monomers are polyetherdiols. They are obtainable in particular by polymerization of ethylene oxide, propylene oxide, butylene oxide, tetrahydrofuran, styrene oxide or epichlorohydrin with themselves, e.g. in the presence of $BF_3$ or through addition of these compounds, optionally in a mixture or successively, onto starter components with reactive hydrogen atoms, such as alcohols or amines, e.g. water, ethylene glycol, propane-1,2-diol, propane-1,3-diol, 1,2-bis(4-hydroxydiphenyl)propane or aniline. Particular preference is given to polytetrahydrofuran with a molecular weight of from 240 to 5000, and especially 500 to 4500.

Polyhydroxyolefins, preferably those with 2 terminal hydroxyl groups, e.g. α,-ω-dihydroxypolybutadiene, α,-ω-dihydroxypolymethacrylate or α,-ω-dihydroxypolyacrylate, are likewise suitable as monomers. Such compounds are known, for example, from EP-A-0 622 378. Further suitable polyols are polyacetals, polysiloxanes and alkyd resins.

The following examples illustrate the invention in more detail.

EXAMPLE 1

1st Step:

Firstly, 120 g of diethylene glycol monomethyl ether (1 mol), which had been carefully purified by distillation, were introduced into a pressurized reactor. After adding 1 g of NaOH, drying was carried out at 90° C. in vacuo. Then, at a temperature of 130° C. and a pressure of about 6 bar, firstly a mixture of 290 g (5 mol) of propylene oxide and 1672 g (38 mol) of ethylene oxide was metered in and, after its complete reaction, evident from a pressure drop, an amount of 232 g (4 mol) of propylene oxide was metered in. Following the complete reaction of the propylene oxide, evident from a drop in pressure, the reaction was stopped by adding acetic acid and the product was analyzed by means of OH number titration and NMR. The OH number was 24 mg KOH/g, corresponding to a molar mass of 2330 g/mol. The distribution of the oxyethylene, oxypropylene chain fractions and also of the methoxy ($CH_3O$—), primary (—$CH_2OH$) and secondary (—$CHCH_3OH$) end groups can be derived from the NMR spectrum:

|  | Functional groups | | | | |
| --- | --- | --- | --- | --- | --- |
|  | $CH_3$—O— | $OCH_2CH_2O$ | $OCH_2CHCH_3O$ | —$CHCH_3OH$ | —$CH_2OH$ |
| Molar ratio, measured by $^1H$ signals | 1 | 38 | 9 | 0.98 | 0.07 |

Step 2:

730 g of the α-hydroxy-Ω-methoxypolyoxyalkylene-polyoxypropylene block copolymer from step 1 having a molar mass of 2330 g/mol and a molar ratio of the oxypropylene units to the oxyethylene units of 19:81 were reacted with ammonia and hydrogen in the presence of an Ni-containing catalyst to give the corresponding amine. The resulting primary amine had a total nitrogen content of 0.60% by weight.

Step 3:

The amine from step 2 was reacted, following removal of the catalyst, with 2 mol equivalents of ethylene oxide (34 g) at 190° C. and a pressure of 4 bar to give the corresponding α-dihydroxyethylamino-Ω-methoxypolyalkylene glycol. The total nitrogen content after the reaction was 0.57% by weight, corresponding to a molar mass of 2456 g/mol. The fraction of tertiary amine was 98.2% by weight. The product was characterized by means of $^1$H-NMR.

| | Functional groups | | | | |
|---|---|---|---|---|---|
| | $CH_3$—O— | $OCH_2CH_2O$ | $OCH_2CHCH_3O$ | —$CH_2N(CH_2CH_2OH)_2$ | —$CH_2OH$ |
| Molar ratio, measured by $^1$H signals | 1 mol | 39 mol | 8.5 mol | 1.05 mol | 2.1 |

EXAMPLE 2

1st Step:

Firstly, 180 g of diethylene glycol monomethyl ether (1.5 mol), which had been carefully purified by distillation, were introduced into a pressurized reactor. After adding 1 g of NaOH, drying was carried out at 90° C. in vacuo. Then, at a temperature of 140° C. and a pressure of about 6 bar, firstly 660 g (15 mol) of ethylene oxide was metered in and, after its complete reaction, evident from a pressure drop, an amount of 262 g (4.5 mol) of propylene oxide was metered in. Following the complete reaction of the propylene oxide, evident from a drop in pressure, the reaction was stopped by adding acetic acid and the product was analyzed by means of OH number titration and NMR.

The OH number was 75 mg KOH/g, corresponding to a molar mass of 748 g/mol. The distribution of the oxyethylene, oxypropylene chain fractions and also of the methoxy ($CH_3O$—), primary (—$CH_2OH$) and secondary (—$CHCH_3OH$) end groups can be derived from the NMR spectrum:

| | Functional groups | | | | |
|---|---|---|---|---|---|
| | $CH_3$—O— | $OCH_2CH_2O$ | $OCH_2CHCH_3O$ | —$CHCH_3OH$ | —$CH_2OH$ |
| Molar ratio, measured by $^1$H signals | 1 | 12 | 3 | 0.96 | 0.05 |

2nd Step:

685 g of the α-hydroxy-Ω-methoxypolyoxyethylene-polyoxypropylene block copolymer from step 1 with a molar mass of 748 g/mol were reacted with ammonia and hydrogen in the presence of an Ni-containing catalyst to give the corresponding amine. The resulting primary amine had a total nitrogen content of 1.78% by weight.

3rd Step:

The amine from step 2 was reacted, following removal of the catalyst, with 2 mol equivalents of ethylene oxide (81 g) at 190° C. and a pressure of 4 bar to give the corresponding α-dihydroxyethylamino-Ω-methoxypolyalkylene glycol. The total nitrogen content after the reaction was 1.6% by weight, corresponding to a molar mass of 875 g/mol. The fraction of tertiary amine was 99% by weight. The product was characterized by means of $^1$H-NMR.

| | Functional groups | | | | |
|---|---|---|---|---|---|
| | CH₃—O— | OCH₂CH₂O | OCH₂CHCH₃O | —CH₂N(CH₂CH₂OH)₂ | —CH₂OH |
| Molar ratio, measured by ¹H signals | 1 | 12 | 3 | 1 | 2.05 |

EXAMPLE 3

Preparation of an Aqueous Polyurethane Dispersion in the Acetone Process 224 g of an adipic acid-diethylene glycol-polyesterdiol (OH number 52.6), 1.34 g of DMPA, 52.5 g of the α-dihydroxyethylamino-Ω-methoxypolyalkylene glycol from example 2, 16.8 g of hexamethylene diisocyanate and 44.2 g of isophorone diisocyanate were reacted at 90° C. in two hours to give a polyurethane prepolymer. The theoretical residual NCO content was 3.10% by weight. The theoretical value, determined by titration, was 2.36% by weight on account of the amine present. The residual NCO content measured in the experiment was 2.18% by weight. 150 g of acetone were added to the prepolymer, which was neutralized with 1 g of triethylamine, cooled to room temperature and dispersed with 650 g of water. The chain extension of the aqueously dispersed prepolymer was carried out with 6.7 g of ethylene diamine, dissolved in 50 g of water. During a subsequent distillation in vacuo, the acetone was removed. This gave a milky-white, thin-liquid and storage-stable polyurethane dispersion with a solids content of 30% by weight, a pH of 8.0 and an average particle diameter of 200 nm (measured using Particle Size Analyzer 90 Plus, Brookhaven Instruments).

EXAMPLE 4

Preparation of an Aqueous Polyurethane Dispersion in the Prepolymer-Ionomer Process 153 g of a polypropylene glycol (OH number 110), 70 g of the α-dihydroxyethylamino-Ω-methoxypolyalkylene glycol from example 2 and 77.4 g of isophorone diisocyanate were reacted with 0.1 g of dibutyltin dilaurate at 75° C. in 2.5 hours to give a polyurethane prepolymer. The theoretical residual NCO content was 3.36% by weight. The theoretical value, determined by titration, was 2.24% by weight on account of the amine present. The residual NCO content measured in the experiment was 2.20% by weight. The prepolymer was cooled to 45° C. and dispersed in 650 g of water. The chain extension of the aqueously dispersed prepolymer was carried out with 7.1 g of ethylenediamine, dissolved in 50 g of water. This gave an orange opaque, thin-liquid and storage-stable polyurethane dispersion with a solids content of 30% by weight, a pH of 8.5 and an average particle diameter of 40 nm.

The invention claimed is:

1. A compound of formula 2

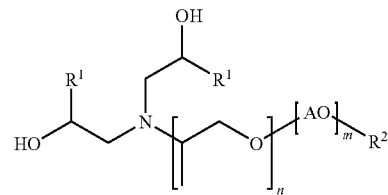

(2)

wherein
$R^1$ is H, methyl or ethyl,
$R^2$ is methyl
A is a $C_2$- to $C_4$-alkylene group,
m is a number from 1 to 400
n is 1, 2, 3, 4 or 5.

2. A compound as claimed in claim 1, in which at least 50 mol % of the radicals (A-O) are oxyethylene radicals —CH₂—CH₂—O—.

3. A compound as claimed in claim 2, in which any non-oxyethylene radicals (A-O) are oxypropylene radicals —CH(CH₃)—CH₂—O—.

4. A compound as claimed in claim 1, in which A is an ethylene group and m is a number from 3 to 300.

5. A compound as claimed in claim 1, in which $R^1$ is H.

6. A compound as claimed in claim 1, in which -(A-O)$_m$—$R^2$ is an oxyalkylene group of the formula —(CH₂—CH₂—O)$_b$—(CH(CH₃)—CH₂—O)$_a$—$R^2$ in which
a is a number from 0 to 300,
b is a number from 3 to 300, and
$R^2$ is as defined in claim 1.

* * * * *